(12) United States Patent
Nagano et al.

(10) Patent No.: US 8,062,204 B2
(45) Date of Patent: Nov. 22, 2011

(54) COIL DEVICE AND MAGNETIC FIELD GENERATING DEVICE

(75) Inventors: Isamu Nagano, Kanazawa (JP); Yoshio Ikehata, Kanazawa (JP)

(73) Assignee: Kanazawa University, Kanazawa-shi (JP)

( * ) Notice: Subject to any disclaimer, the term of this patent is extended or adjusted under 35 U.S.C. 154(b) by 1062 days.

(21) Appl. No.: 11/578,951

(22) PCT Filed: Apr. 22, 2005

(86) PCT No.: PCT/JP2005/007721
§ 371 (c)(1),
(2), (4) Date: Oct. 4, 2007

(87) PCT Pub. No.: WO2005/104622
PCT Pub. Date: Nov. 3, 2005

(65) Prior Publication Data
US 2008/0114429 A1      May 15, 2008

(30) Foreign Application Priority Data
Apr. 23, 2004   (JP) ................. 2004-128364

(51) Int. Cl.
*A61N 2/02*        (2006.01)
(52) U.S. Cl. .............................. 600/13; 600/9
(58) Field of Classification Search ............... 600/9–15; 219/632, 677; 174/15.1
See application file for complete search history.

(56) References Cited

U.S. PATENT DOCUMENTS
3,946,349 A * 3/1976 Haldeman, III ................. 336/62
(Continued)

FOREIGN PATENT DOCUMENTS
JP          A 59-211985        11/1984
(Continued)

OTHER PUBLICATIONS
Apr. 26, 2011 Office Action issued in Japanese Patent Application No. 2006-512606 (with English-language translation).

*Primary Examiner* — Charles A Marmor, II
*Assistant Examiner* — Catherine E Burk
(74) *Attorney, Agent, or Firm* — Oliff & Berridge, PLC

(57) ABSTRACT

Problems to be solved: to provide a coil device and a magnetic field generating device with reduced energy loss that are suitable for use in the thermotherapy method.
Means for solving the problem: a coil device according to the present invention can be used in a magnetic field generating device for the thermotherapy method in which a magnetic flux is irradiated to the patient to selectively heat a specific portion of the patient. Said coil device is a bread-shaped coil device having a current path extending in the shape of a spiral in a substantially same plane, said current path comprising a hollow cylindrical member (10) of a nonmagnetic material inside which a space is formed and a plurality of conductive wires (11, 12) covered with an insulation material on the peripheries thereof. In the present invention, the current path comprising a plurality of conductive wires covered with an insulation material which are arranged in a circle, energy loss caused by the skin effect and energy loss caused by the line capacity can be reduced, making it possible to generate a strong magnetic field. Also, by using the hollow cylindrical member (10), it is possible to easily configure a current path in a predetermined diameter and to inhibit increase in temperature of the coil (3) to avoid fluctuation of the resonance frequency of the resonance circuit. With this, a magnetic field generating device that is suitable for use in thermotherapy, particularly cancer therapy, can be realized.

5 Claims, 4 Drawing Sheets

U.S. PATENT DOCUMENTS

| | | | | |
|---|---|---|---|---|
| 5,208,433 A * | 5/1993 | Hellegouarc'h et al. | ..... | 219/674 |
| 5,430,274 A * | 7/1995 | Couffet et al. | ................ | 219/677 |
| 5,477,035 A * | 12/1995 | Matsumoto et al. | .......... | 219/635 |
| 6,049,042 A | 4/2000 | Avellanet | .................... | 174/128.1 |
| 6,741,152 B1 * | 5/2004 | Arz et al. | ...................... | 335/300 |
| 7,045,704 B2 * | 5/2006 | Areskoug | ................... | 174/15.1 |
| 2001/0031906 A1 * | 10/2001 | Ishikawa et al. | ................ | 600/13 |
| 2002/0103411 A1 * | 8/2002 | Bailey et al. | ....................... | 600/9 |
| 2002/0117320 A1 * | 8/2002 | Hyogo | ......................... | 174/68.1 |
| 2003/0216729 A1 * | 11/2003 | Marchitto et al. | .............. | 606/41 |
| 2005/0103519 A1 * | 5/2005 | Brandsberg et al. | ....... | 174/125.1 |
| 2007/0215606 A1 * | 9/2007 | Albaugh | ...................... | 219/677 |

FOREIGN PATENT DOCUMENTS

| | | |
|---|---|---|
| JP | A 6-36869 | 2/1994 |
| JP | A 9-168484 | 6/1997 |
| JP | A 9-245949 | 9/1997 |
| JP | A 11-102781 | 4/1999 |
| JP | A 2002-360712 | 12/2002 |
| JP | A 2003-115368 | 4/2003 |
| JP | A 2003-205040 | 7/2003 |
| JP | A 2004-79318 | 3/2004 |
| WO | WO 95/22239 A1 | 8/1995 |
| WO | WO 01/84571 A1 | 11/2001 |
| WO | WO 0184571 A1 * | 11/2001 |

* cited by examiner (A)

(B)

COIL DEVICE AND MAGNETIC FIELD GENERATING DEVICE

FIELD OF THE INVENTION

The present invention relates to a coil device, particularly to a coil device with drastically reduced energy loss. The present invention further relates to a magnetic field generating device used for induction heating therapy, particularly to a magnetic field generating device with reduced energy loss.

BACKGROUND OF THE INVENTION

The thermotherapy (hyperthermia) method is attracting attention as a method for cancer therapy. By this thermotherapy method, attention is focused upon the fact that a cancer cell or a cancerous tissue is more vulnerable to heat than a healthy cell. By heating the cancer-affected portion for example to 43 degree C. for a certain length of time, the cancer lesion can selectedly be necrotized. In this thermotherapy method, an aqueous sol of magnetic fluid such as a complex of dextran or its derivative and magnetic iron oxide is injected into the affected portion, to which a strong magnetic field is applied from outside to selectively heating the cancer lesion (see Japanese Patent Laid-open Publication No. 2002-360712).

In order to inductively heat the magnetic material having been injected into the affected portion of the patient, it is necessary to irradiate a strong magnetic flux from outside to the affected portion by using a magnetic field generating device. As a preferred magnetic field generating device for this inductive heating is used a device comprising a series resonant circuit of a coil as a magnetic field generating means and a resonant capacitor being connected to the secondary side of the transformer, in which a large current of high frequency is applied to the coil to generate a magnetic field. Since the intensity of the magnetic field generated by the coil decreases progressively with distance, it is preferable to place the source of the magnetic field as close as possible to the affected portion. For this reason, a bread-shaped coil is used as a coil for generating a magnetic field, whose current path is formed into a spiral shape in a same plane.

As an another preceding example is disclosed a device for heating the cancer-affected portion by irradiating a high-density magnetic flux, in which along the periphery of a solenoid coil are provided dual coils, so that magnetic flux density is enhanced with the outer coil (the reinforcement coil) (see Japanese Patent Laid-open Publication No. 2003-205040). Further, a technique for eliminating a skin effect in a bread-shaped spiral coil comprising entwisted conductive wires is disclosed, in which a conductive wire in the shape of a right-hand spiral and a conductive wire in the shape of a left-hand spiral are doubly arranged on the periphery thereof as coils (see Japanese Patent Laid-open Publication No. 2003-115368). In addition, as a technique for cooling a coil comprising a circular cylinder of an insulation material and a litz wire folded about the periphery of the circular cylinder is disclosed, in which a cold airstream is blown into the circular cylinder (see Japanese Patent Laid-open Publication No. 1997-168494). Also, a technique of providing ferrite at the bottom of a coil to shield an electromagnetic wave is disclosed (see Japanese Patent Laid-open Publication No. 1997-245949).

DISCLOSURE OF THE PRESENT INVENTION

Problems to be Solved

In order to heat the magnetic fluid having been injected into the affected portion to around 43 degree C., it is necessary to apply large current of high frequency to a resonance circuit connected to the secondary side of a transformer. In applying large current of high frequency to a bread-shaped coil as a magnetic field generating means, however, energy loss caused by the skin effect induced in the current path becomes problematic. According to an analysis carried out by the inventor of the present invention, in the case of applying a current having a high frequency of 400 kHz to a metallic conductor, the current is substantively flowing only in a width of 0.1 mm, leading to increased resistance. Consequently, too much energy will be lost because of Joule heat produced by the coil current. Also, the inductance of the resonance circuit varies as temperature of the coil increases, to limit the amount of current that can be provided to the secondary side of the transformer.

The present invention is intended to provide a coil device with drastically reduced loss caused by the skin effect of the current path and with improved energy loss. Also, the present invention is further intended to provide a magnetic field generating device with reduced energy loss, which is suitable for thermotherapy (particularly cancer therapy).

Means for Solving the Problems

A coil device according to the present invention is a bread-shaped coil device comprising a current path extending in a spiral shape in a substantially same plane, said current path comprising a hollow cylindrical member of a nonmagnetic material inside which a space is formed and a plurality of conductive wires covered with an insulation material that is arranged along the periphery of said hollow cylindrical member, each of said conductive wires in arranged in such a way as to form a circle in a predetermined diameter, seen from the cross-sectional direction of the current path.

In the thermotherapy method for selectively heating the affected portion by injecting a magnetic fluid into the affected portion and applying a magnetic field from outside, it is necessary to form a strong magnetic field at the affected portion by supplying large current of high frequency to the coil device. However, by supplying large current of high frequency to a conductor, the skin effect is brought about to waste a large mass of energy. It is conceivable to use a bundle of conductive wires of small diameter covered with an insulation material (a litz wire) as a current path of the coil. When using the litz wire as a conductor included in the coil, the effect of reducing the skin effect can be observed. After carrying out various experiments and analyses using the litz wire, however, the inventor of the present invention has found the fact that a line capacity, the capacity between the conductive wires included in each litz wire, has a strong influence to cause prominent energy loss, even though the skin effect can be reduced slightly.

According to the result of a further analysis having been carried out by the inventor of the present invention, it has been found that with the use of a bundle of conductive wires with insulation provided on the peripheries thereof, there still remains the skin effect. Seeing the current path as a whole, the amount of current is smaller in the inner conductor to increase in the outer conductor, so that a massive amount of current is passing in the outermost conductor. Further, after a careful and detailed analysis of the line capacity, it has been found that the line capacity decreases drastically as the inner conductor in the bundle of conductors is removed. Only with the outermost conductor energy loss caused by the line capacity becomes so small that it can be ignored. Based on the result of these analyses, an arrangement of conductive wires is adopted, in which the conductive wires are arranged to form a circle in a predetermined diameter. By using a bundle of conductive wires arranged in a circle as a current path of a coil in such a way as explained above, energy loss can drastically be reduced.

Moreover, by arranging a multitude of conductive wires along the periphery of a hollow cylindrical member, a current path in the predetermined diameter can easily be configured. In addition, by circulating the air in the space inside the hollow cylindrical member, increase in temperature of the coil can be inhibited to avoid fluctuation in the resonance frequency of the resonance circuit. It is preferable to configure the bundle of conductive wires that is to be arranged along the periphery of the hollow cylindrical member to be onefold or twofold. It may be the best way to singly fold conductors in a small diameter, but energy loss caused by the line capacity does not increase notably even when conductors are doubly folded.

A preferred embodiment of the coil device of the present invention can be characterized in that a cooling agent is circulated inside the hollow cylindrical member. When large current of high frequency is supplied, it is difficult to remove influence of the skin effect completely, so that Joule heat is inevitably generated. With a large amount of Joule heat, there occurs fluctuation in the resonance frequency of the series resonance circuit, which will lead to reduced energy to be transmitted to the secondary side of the transformer, as well as other problems brought about by heat. The present embodiment therefore brings solutions to the problem of fluctuation in the resonance frequency by circulating a cooling agent inside the hollow cylindrical member to maintain the coil itself at constant temperature.

A modified embodiment of the coil device of the present invention can be characterized in that the current path comprises a hollow cylindrical member of a nonmagnetic material having a space formed inside and a plurality of conductive wires that are covered with an insulation material and arranged inside the hollow cylindrical member, and a cooling agent is circulated inside said hollow cylindrical member. The cooling agent that is circulating inside the hollow cylindrical member directly cools off the conductive wires as a heat source. Temperature of the coil itself can thus be held constant to solve the problem of fluctuation of the resonance frequency.

A magnetic field generating device according to the present invention is a magnetic generator that can be used for the thermotherapy method, comprising a series resonance circuit of a magnetic field generating coil connected to the secondary side of the transformer and a resonance condenser, said magnetic field generating coil comprising a bread-shaped coil device having a current path extending in the shape of a spiral in the coil plane, said bread-shaped coil device comprising a hollow cylindrical member of a nonmagnetic material and a plurality of conductive wires that are arranged on the periphery of the hollow cylindrical member and covered with an insulation material, each conductive wire being arranged in such a way as to form a circle in a predetermined diameter, see from the cross-sectional direction of the current path.

A preferred embodiment of the magnetic field generating device of the present invention can be characterized in that a core plate of a high-permeability material having an outer diameter that is equal to or larger than the outermost diameter of the bread-shaped coil is arranged on one side of the coil plane of the bread-shaped coil device. In the case of using a bread-shaped coil as a magnetic field generating coil, a magnetic field is generated towards the both sides of the coil plane, so that the portion of magnetic field generated on one side cannot be used for therapy. Thus, in the present embodiment, a core plate of a high-permeability material is arranged on the other side of the coil than the side facing the affected portion. With this, magnetic reluctance drastically decreases on the opposite side of the affected portion, while magnetic field generated towards the affected portion increases further. Energy loss can drastically be reduced in this way. Thus, by using together the coil device of the present invention and a core plate, energy loss can be reduced the further.

A preferred embodiment of the magnetic field generating device of the present invention can be characterized in that a bread-shaped coil device and a core plate are arranged inside a case of a nonmagnetic material and a cooling agent is circulated in the case to cool off the coil device and the core plate. By cooling off the bread-shaped coil and the core plate as a whole, it is possible to hold the inductance of the coil substantially constant, solving the problem of fluctuation of the resonance frequency of the resonance circuit.

DESCRIPTION OF THE PREFERRED EMBODIMENTS

Figure 1:
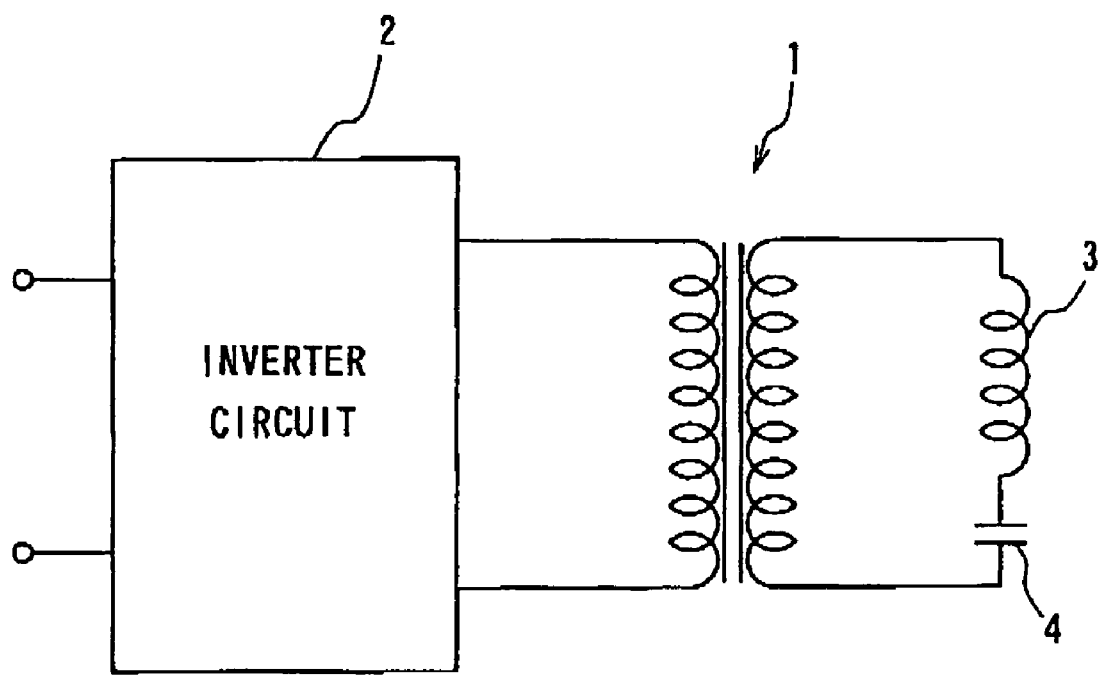
FIG. 1 is a diagram showing a circuit constitution of the magnetic field generating device of the present invention.

FIG. 1 is a diagram showing a circuit constitution of the magnetic field generating device of the present invention. An inverter circuit 2 comprising a semiconductor switching element is connected to the primary side of a transformer 1 to generate an alternate output of a predetermined frequency. A resonance circuit comprising a coil 3 as a magnetic field generating means and a resonance condenser 4 series-connected to each other is connected to the secondary side of the transformer 1. The alternate output is configured to have a substantially same frequency as the resonance frequency of the series resonance circuit on the secondary side. The magnetic field generating device transmits energy from the primary side to the secondary side through electromagnetic induction, generates an alternate magnetic field from the coil 3 and irradiates a magnetic flux to the affected portion of the patient. To the coil 3 on the secondary side is applied for instance a current of 300 A and 5 kV having a frequency of several hundred kHz. As an example, a coil of an inductance of 4 µH can be used as a coil 3, and a condenser circuit comprising three groups of condensers that are parallel-connected can be used as a resonance condenser 4, each group thereof having five series-connected condensers of 0.04 µF whose withstand pressure is 1,000 V.

Figure 2:
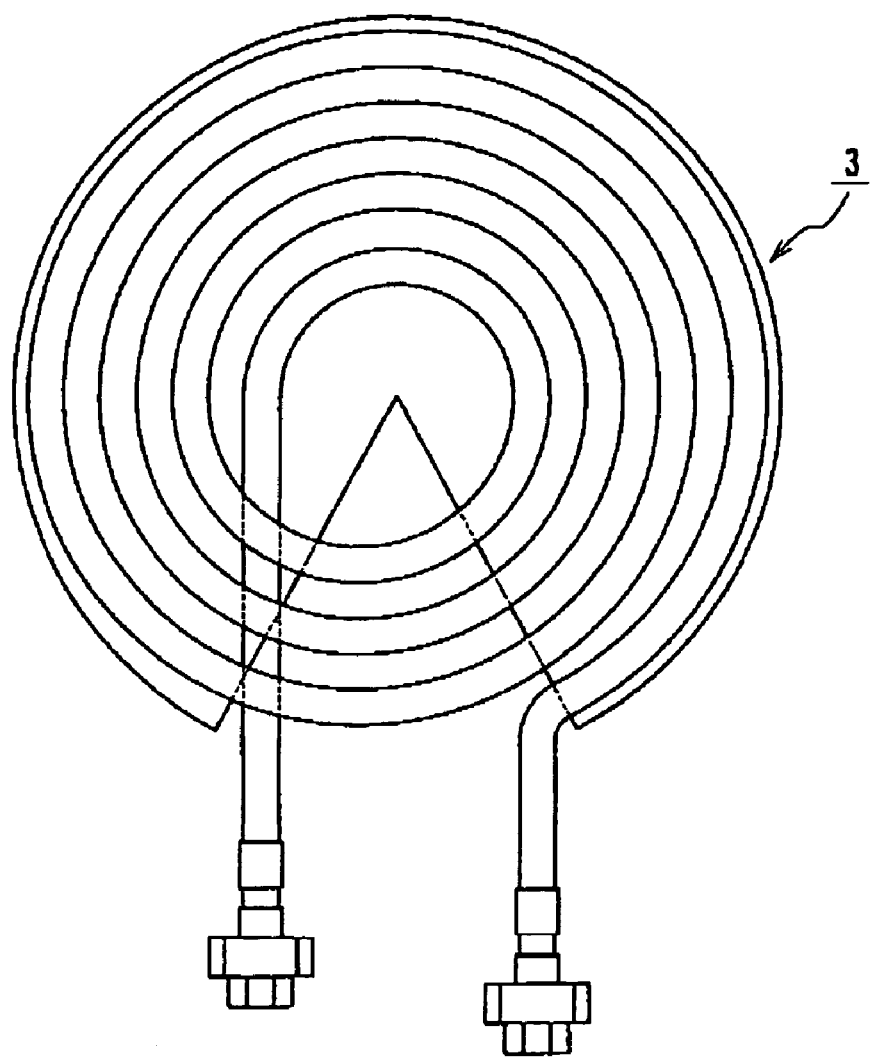
FIG. 2 is a diagram showing an example of the coil device of the present invention.
Figure 2:
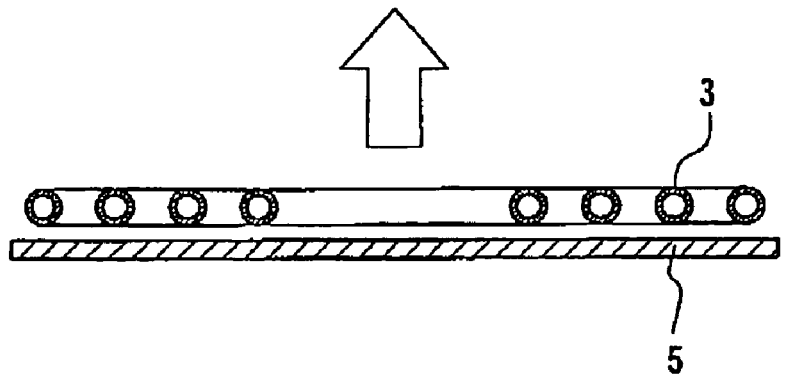

FIG. 2(A) and FIG. 2(B) show a plan view and a cross-sectional view on an example of the magnetic field generating coil. According to the present invention, a bread-shaped coil device having a current path formed in a spiral shape in a same plane (the coil plane) is used as a magnetic field generating coil. On the bottom side of the bread-shaped coil 3 is provided a core plate 5 of a high-permeability material. Ferrite can be used for instance as a high-permeability material.

Figure 3:
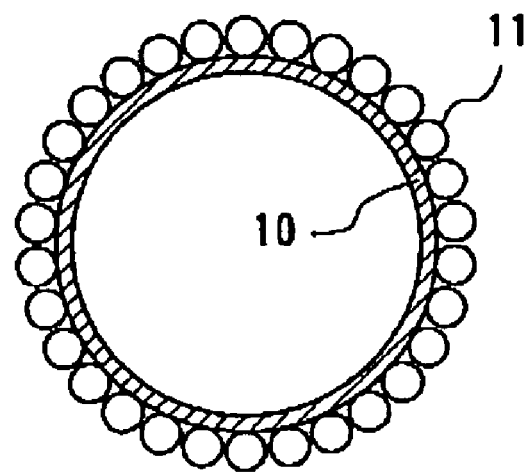
FIG. 3 is a cross-sectional view showing a constitution of the current path.

FIG. 3 shows a cross-sectional view on the current path of the coil 3. The current path of the present invention comprises a hollow cylindrical member 10 of a nonmagnetic material inside which a space is formed and a bundle of conductive wires 11 arranged on a circle along the periphery of the hollow cylindrical member 10. The bundle of the conductive wires 11 is provided with a twist along the direction of the current and can correspond to a helical current path. The coil current passes evenly in each conductive wire 11. By arranging onefoldly the conductive wires 11 along the periphery of the hollow cylindrical member 10 in this way, it is possible not only to reduce the skin effect but also to cut down energy loss caused by the line capacity among the conductive wires 11, which working together can improve energy loss drastically. Also, it is easy to configure a current path of any predetermined diameter. Further, by circulating an airstream in the space formed inside the hollow cylindrical member 10, it is possible to reduce increase in temperature of the coil 3, inhibiting fluctuation of the resonance frequency of the resonance circuit. The increase in temperature of the coil can further be reduced, and the fluctuation of the resonance frequency of the resonance circuit can further be inhibited if a cooling agent is circulated inside the hollow cylindrical member 10.

Figure 4:
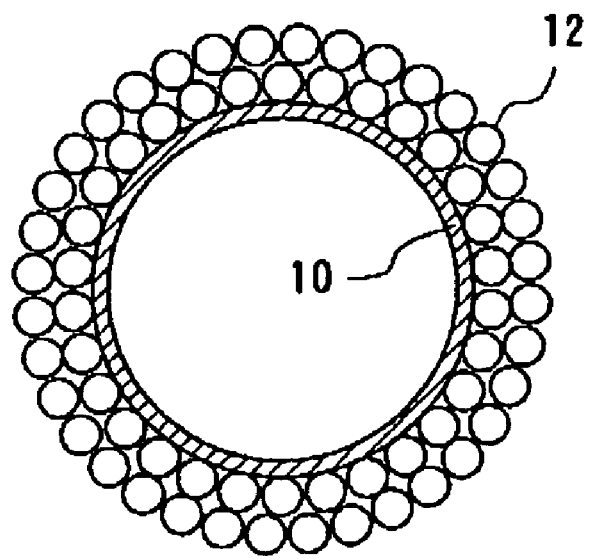
FIG. 4 is a cross-sectional view showing a modified example of the current path.

FIG. 4 shows a modified example of the current path. In this example, the current path comprises the hollow cylindrical member 10 and a bundle of conductive wires 12 twofoldly arranged in a circle along the periphery of the hollow cylindrical member 10. According to the result of an analysis carried out by the inventor of the present invention, increase in the line capacity is only marginal and does not add to energy loss if the conductive wires are doubly folded.

Now, we will go back again to FIG. 2(A) and FIG. 2(B), which will help explaining the function and the effect of the core plate 5. A bread-shaped coil generates a magnetic field towards both sides of the coil plane. It is, however, only the magnetic field generated from one side that is applied to the affected area, while the portion of magnetic field generated from the other side is simply wasted. That is to say, a half of the magnetic field generated from the coil 3 will energetically be lost. In this example, therefore, as shown in FIG. 2(B), a core plate 5 of high-permeability material such as ferrite is arranged substantially parallel to the coil plane on the opposite side of the affected area towards which a magnetic field is applied. The outer diameter of the core plate 5 is made equal to or larger than the outermost diameter of the coil 3. Since magnetic reluctance of the core plate 5 of a high-permeability material is much smaller than that of the air, the magnetic flux applied to the affected area increases further to reduce energy loss drastically.

Figure 5:
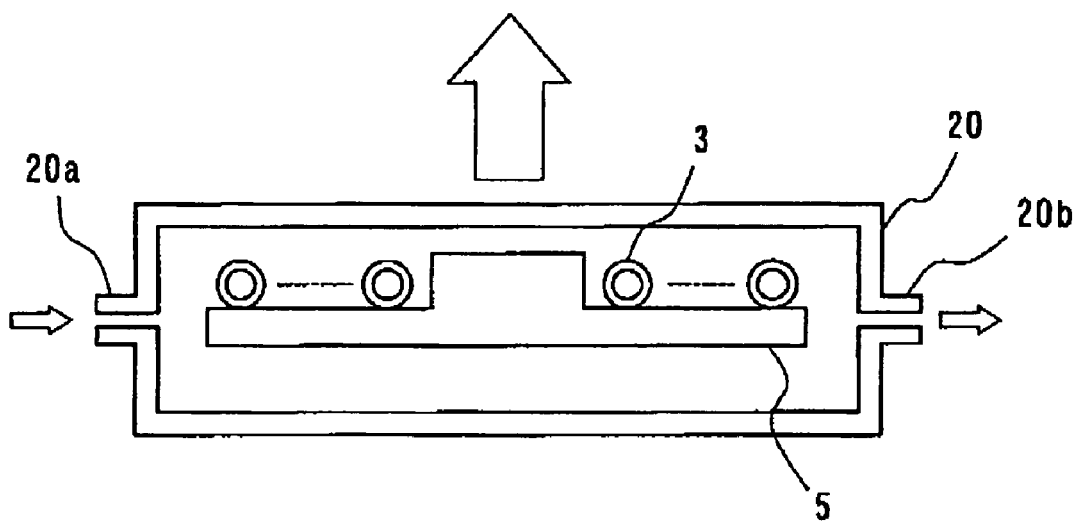
FIG. 5 is a diagram showing an example of the magnetic field generating device of the present invention.

FIG. 5 is a cross-sectional view showing an example of the magnetic field generating device of the present invention. In this example, a magnetic field generating coil 3 and the core plate 5 are arranged in a case 20 of a nonmagnetic material. The case 20 comprises an inlet 20a and an outlet 20b, which are in use for circulating a cooling agent. As a cooling agent, for example, silicone oil, water or fluorocarbon cooling agent can be used. Due to the coil 3 and the core plate 5 arranged in a case inside which the cooling agent is circulated, increase in temperature of the coil 3 can be inhibited. Further, since inductance of the coil 3 can be held substantially constant, fluctuation of the resonance frequency of the resonance circuit can be avoided.

The diameters of the conductive wires 11 and the conductive wires 12 as shown in FIG. 3 and FIG. 4 preferably range from 0.06 mm to 0.1 mm. This is because by using as small a diameter as 0.1 mm, loss caused by the skin effect of the current path can be reduced, and the energy loss can be improved. In addition, the above described range of diameter is standard from a perspective of manufacturing a bread-shaped coil 3. If the diameter is smaller than 0.06 mm, for example 0.05 mm or 0.04 mm, although it is possible to achieve an equivalent effect as mentioned above, there will be difficulties in manufacturing. On the other hand, if the diameter is made larger than 0.1 mm, loss caused by the skin effect and energy loss may be reduced to a certain extent, but not sufficiently.

The numbers of the conductive wires 11 and 12 preferably range from 1,000 to 100,000. This is because, if the number is larger than 1,000, loss caused by the skin effect of the current path can be reduced, and energy loss can be improved sufficiently. In addition, the above described range of the number can be considered reasonable from a perspective of manufacturing a bread-shaped coil 3. The number being larger than 100,000, although it is possible to achieve an equivalent effect as mentioned above, there will be difficulties in manufacturing. On the other hand, the number being smaller 1,000, loss caused by the skin effect and energy loss may be reduced to a certain extent, but not sufficiently.

The hollow cylindrical member 10 as shown in FIG. 3 and FIG. 4 is preferably provided with an inner diameter ranging from 5 mm to 40 mm. This is because, if the diameter is smaller than 5 mm, it is difficult to achieve a sufficient cooling effect, there being no point in forming a space in the cylindrical member. On the other hand, if the diameter is larger than 40 mm, there will be difficulties in manufacturing, although it is possible to achieve the desired cooling effect.

The present invention is not limited to the above described examples. Various changes and modifications are possible within the scope of the invention. For example, although the coil device used for the thermotherapy method has been explained above, it can as well be used for various purposes other than the thermotherapy method. For example, the present invention can be applied for magnetic field generating devices including a high-frequency quenching device and a plasma generator, which generate a strong magnetic field by applying large current of high frequency.

In the above described embodiments, the bundles of the conductive wires 11 and 12 are arranged in a circle along the periphery of the cylindrical member 10. However, it is also possible to arrange the conductive wires inside the cylindrical member 10. In this case, it is possible to directly cool off the conductive wires 11 and 12 by circulating the air or a cooling agent inside the cylindrical member 10. With this, increase in temperature of the coil 3 can further be inhibited, and fluctuation of the resonance frequency of the resonance circuit can further be avoided.

The invention claimed is:

1. A magnetic field generating device used for a thermotherapy method comprising:
   a series resonance circuit having a magnetic field generating coil and a resonance condenser, said magnetic field generating coil comprising a disc-shaped coil device comprising a current path extending in a shape of a spiral in substantially a single plan, said current path comprising a hollow cylindrical member of a nonmagnetic material inside which a space is formed and a plurality of conductive wires covered with an insulation material are arranged on a periphery of said hollow cylindrical member, wherein:
   each conductive wire is arranged in a circumference of a circle in a predetermined diameter seen from a cross-sectional direction of the current path,
   said conductive wires are provided with a twist along a line of a central axis of the current path, the diameters of said conductive wires range from 0.06 mm to 0.1 mm, the inner diameter of said hollow cylindrical member ranges from 5 mm to 40 mm, a cooling agent is circulated inside said hollow cylindrical member, a core plate of a high permeability material having an outer diameter equal to or larger than an outermost diameter of said disc-shaped coil is arranged on one side of the plane of said disc-shaped coil device, and said magnetic field generating device is used for the thermotherapy method in which a magnetic flux is irradiated from outside to a patient to selectively heat a specific portion of the patient.

2. The magnetic field generating device according to claim 1, wherein said conductive wires are arranged onefoldly or twofoldly along the periphery of the hollow cylindrical member.

3. The magnetic field generating device according to claim 1, wherein the number of the conductive wires arranged on the periphery of said hollow cylindrical member ranges from 1,000 to 100,000.

4. The magnetic field generating device according to claim 1, wherein said disc-shaped coil device and said core plate are arranged inside a case of a nonmagnetic material in which a cooling agent is circulated to cool off the coil device and the core plate.

5. The magnetic field generating device according to claim 1, wherein said conductive wires are arranged twofoldly along the periphery of the hollow cylindrical member.

* * * * *